US012667580B2

(12) United States Patent
Lee et al.

(10) Patent No.: US 12,667,580 B2
(45) Date of Patent: Jun. 30, 2026

(54) RETINOIC ACID PRECURSOR AND ANTICANCER DRUG COMPOSITION COMPRISING SAME

(71) Applicant: INDUSTRIAL COOPERATION FOUNDATION JEONBUK NATIONAL UNIVERSITY, Jeonju-si (KR)

(72) Inventors: Dong Won Lee, Jeonju-si (KR); Eun Kyeong Jung, Suncheon-si (KR)

(73) Assignee: INDUSTRIAL COOPERATION FOUNDATION JEONBUK NATIONAL UNIVERSITY, Jeonju-si (KR)

( * ) Notice: Subject to any disclaimer, the term of this patent is extended or adjusted under 35 U.S.C. 154(b) by 270 days.

(21) Appl. No.: 18/291,074

(22) PCT Filed: Jul. 20, 2022

(86) PCT No.: PCT/KR2022/010593
§ 371 (c)(1),
(2) Date: Jan. 22, 2024

(87) PCT Pub. No.: WO2023/003343
PCT Pub. Date: Jan. 26, 2023

(65) Prior Publication Data

US 2024/0261309 A1 Aug. 8, 2024

(30) Foreign Application Priority Data

Jul. 21, 2021 (KR) ........................ 10-2021-0095512

(51) Int. Cl.
*A61K 31/69* (2006.01)
*A61K 9/14* (2006.01)
(Continued)

(52) U.S. Cl.
CPC ................ *A61K 31/69* (2013.01); *A61K 9/14* (2013.01); *A61K 9/146* (2013.01); *A61K 9/5146* (2013.01);
(Continued)

(58) Field of Classification Search
None
See application file for complete search history.

(56) References Cited

U.S. PATENT DOCUMENTS

2012/0149663 A1 6/2012 Brown et al.
2015/0125533 A1* 5/2015 Sallam .................... A61P 33/00 424/490

FOREIGN PATENT DOCUMENTS

DE 4032187 A1 4/1992
EP 2420228 A1 2/2012
(Continued)

OTHER PUBLICATIONS

Jung et al ("H2O2-activatable hybrid prodrug nanoassemblies as a pure nanodrug for hepatic ischemia/reperfusion injury", Biomaterials, vol. 284 (Apr. 2022) 121515, p. 1-11, as obtained from the website: https://www.sciencedirect.com/science/article/pii/S0142961222001545?via%3Dihub ) (Year: 2022).*
(Continued)

*Primary Examiner* — Sin J Lee
(74) *Attorney, Agent, or Firm* — Bridgeway IP Law Group, PLLC; Jihun Kim

(57) ABSTRACT

A retinoic acid prodrug to which a boron functional group having a structure represented by chemical formula 1 is bound is described. The retinoic acid prodrug self-assembles to form nanoparticles. Therefore, an anticancer drug composition comprises the same as an active ingredient. According to the retinoic acid prodrug, targeted therapy of tumor cells is possible through the synergistic anticancer effect of
(Continued)

retinoic acid and the boron functional group and the surface modification of particles. In particular, the retinoic acid prodrug enables a drug loading of 100 wt %, and thus can provide an effective anticancer drug.

11 Claims, 19 Drawing Sheets

(51) Int. Cl.

| | |
|---|---|
| ***A61K 9/51*** | (2006.01) |
| ***A61K 31/203*** | (2006.01) |
| ***A61K 31/222*** | (2006.01) |
| ***A61K 31/232*** | (2006.01) |
| ***A61P 35/00*** | (2006.01) |
| ***C07F 5/02*** | (2006.01) |

(52) U.S. Cl.

CPC .......... *A61K 31/203* (2013.01); *A61K 31/222* (2013.01); *A61K 31/232* (2013.01); *A61P 35/00* (2018.01); *C07F 5/02* (2013.01); *C07F 5/025* (2013.01); *C07F 5/027* (2013.01)

(56) References Cited

FOREIGN PATENT DOCUMENTS

| | | | |
|---|---|---|---|
| KR | 10-2004-0096570 | A | 11/2004 |
| KR | 10-2015-0081415 | A | 7/2015 |
| KR | 10-1846773 | B1 | 4/2018 |

OTHER PUBLICATIONS

Jung, E. et al. "Self-deliverable and self-i1mnolative prodmg nanoassemblies as tumor targeted nanomedicine with triple cooperative anticancer actions", Biomaterials. 2022, Aug. 2022, inner pp. 1-12, vol. 287, thesis No. 121681, published online: Jul. 18, 2022.

* cited by examiner

RETINOIC ACID PRECURSOR AND ANTICANCER DRUG COMPOSITION COMPRISING SAME

TECHNICAL FIELD

The present invention relates to a retinoic acid prodrug and an anticancer drug composition comprising the same, and presents a model for effectively utilizing the anticancer effect of retinoic acid.

BACKGROUND ART

Retinoic acid (RA) is a type of active metabolite of vitamin A, plays an important role in cell growth and differentiation, and is used in the treatment of acute promyelocytic leukemia. In addition, as it has been reported that retinoic acid exhibits an anticancer effect that kills cancer cells along with an antioxidant effect, interest in its application is increasing.

However, retinoic acid has a significantly lower anticancer effect compared to existing anticancer drugs, and this limits its use as an independent treatment drug, and it causes toxicity to normal cells upon its administration in high doses. In addition, due to its low solubility and absence of capability to target tumors, the development of an effective drug delivery technology is required to develop it as an anticancer treatment drug.

Cancer cells produce a large amount of reactive oxygen species (ROS), such as hydrogen peroxide ($H_2O_2$), which act as a messenger in cell signaling pathways and also induce tumor growth (Noh, J. et. al., Amplification of oxidative stress by a dual stimuli-responsive hybrid drug enhances cancer cell death. Nature Communications 2015, 6, 6907. et al.; and 1). An excessive amount of ROS causes oxidative damage to cancer cells, and even kill cells. Therefore, cancer cells are equipped with a powerful antioxidant defense system to offset the harmful effects of ROS. In particular, glutathione (GSH), which is the most abundant antioxidant in cells, acts as a scavenger of oxygen free radicals and detoxifies xenobiotics (Yoo, D. et. al., Glutathione-Depleting Pro-Oxidant as a Selective Anticancer Therapeutic Agent. ACS Omega 2019, 4, 10070-10077). Many studies have shown that an excess amount of GSH promotes tumor growth and gives cancer cells resistance to treatment. Therefore, depletion of intracellular GSH weakens the antioxidant capacity of cancer cells, thereby making them vulnerable to chemotherapeutic agents.

Boronic acid and boronate linking groups specifically combine with hydrogen peroxide ($H_2O_2$) to form a quinone methide (QM) intermediate, and QM exhibits an anticancer effect by removing GSH, thereby amplifying intracellular oxidative stress and killing cancer cells. In addition, QM reacts with nucleophilic water to generate hydroxybenzyl alcohol (HBA), which exhibits an anticancer effect by preventing the migration or invasion of cancer cells and inhibiting the expression of vascular endothelial growth factor (VEGF) in cancer cells.

In the last two decades, numerous nanocarriers have been developed as drug carriers, and they have been used to deliver hydrophobic anticancer drugs to tumor cells. However, drug carrier-mediated drug delivery has disadvantages such as low drug loading capacity, early drug release, and complexity of scale-up. In addition, most drug carriers act as excipients or do not play any therapeutic role, and they may induce toxicity and immunogenicity during degradation and metabolism.

Self-assembling prodrug based drug self-delivery is drawing attention as a new paradigm in the field of controlled drug delivery for highly efficient anticancer treatment. In drug self-delivery, the drug has a nanometer size and achieves intracellular delivery on its own without a carrier mixed with an additional excipient.

Self-assembly is the formation of nanostructures by effective self-assembly of small molecules through various nanocovalent interactions such as hydrophobic interactions, van der Waals interactions, and pi-pi stacking.

A prodrug is defined as a bioreversible inactive compound that is converted to an active drug upon administration to exhibit its therapeutic activity without toxic side effects.

Self-assembling prodrug based drug self-delivery is a combination of a prodrug and molecular self-assembly and has been realized by accurately controlling the molecular structure of a prodrug. A key design feature of self-assembling prodrugs is amphiphilic balance. They have both hydrophobic and hydrophilic regions and thus can spontaneously assemble in an aqueous environment. As a result, prodrug self-assembly can protect a drug from rapid exhaustion and inhibit early release of the drug. In addition, self-assembling prodrugs play a unique role in terms of high drug loading efficiency of 100% and simple manufacturing process.

An example of a self-assembling prodrug for drug self-delivery is a prodrug amphiphile that binds hydrophilic irinotecan to hydrophobic chlorambucil to form a nanostructure through self-assembly, which realized drug self-delivery without any carrier (Huang, P. et. al., Combination of Small Molecule Prodrug and Nanodrug Delivery: Amphiphilic Drug-Drug Conjugate for Cancer Therapy. Journal of the American Chemical Society 2014, 136, 11748-11756.).

The inventors of the present application made efforts to develop an effective composition for anticancer treatment using retinoic acid and boronic acid or boronate linking groups, and thereby accomplished the present invention.

DETAILED DESCRIPTION OF THE INVENTION

Technical Problem

An object of the present invention is to provide a means to effectively use retinoic acid in anticancer treatment, wherein retinoic acid has limitations in its application to anticancer treatment, and in particular, to provide a means to target and treat tumor cells.

In addition, another object of the present invention is to provide a means for utilizing an anticancer effect of boronic acid or boronate linking groups.

Technical Solution

The present invention provides a boronate retinoic acid prodrug (RABA) to which a boron functional group is bonded, having the structure represented by Formula 1 below:

[Formula 1]

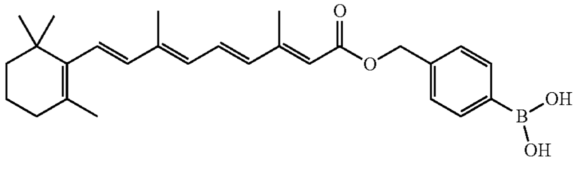

The retinoic acid prodrug may form nanoparticles through self-assembly.

The nanoparticles are formed by nano-precipitating RABA in a solvent.

The nanoparticles may be composed of 100% by weight of RABA.

The surface of the nanoparticles may be coated with γ-polyglutamic acid (γPGA).

The nanoparticles may target cancer cells in which gamma glutamyl transferase (GGT) is overexpressed.

The retinoic acid prodrug produces quinone methide (QM) in the presence of $H_2O_2$.

The retinoic acid prodrug produces hydroxybenzyl alcohol (HBA) in the presence of $H_2O_2$.

The retinoic acid prodrug depletes $H_2O_2$ and glutathione (GSH).

The retinoic acid prodrug inhibits tumor growth.

The present invention provides an anticancer composition including the retinoic acid prodrug as an active ingredient.

Advantageous Effects

According to the present invention, retinoic acid can be effectively used for anticancer treatment. In other words, an anticancer effect may be improved by the synergistic effect of retinoic acid and boron functional groups, and tumor cells may be targeted and treated through surface modification. In particular, since 100% by weight of the nanoparticles of the present invention can be prepared to be composed of a drug having an anticancer effect, there are advantages that the anticancer effect can be maximized, and tumors can be targeted without a separate drug delivery system.

DESCRIPTION OF THE DRAWINGS

FIG. 5B shows a SEM photograph taken after self-assembly reaction of RA and Compound 2.

BEST MODE

The present invention provides a boronate retinoic acid prodrug (RABA) to which a boron functional group is bonded, having the structure shown in Formula 1 below:

[Formula 1]

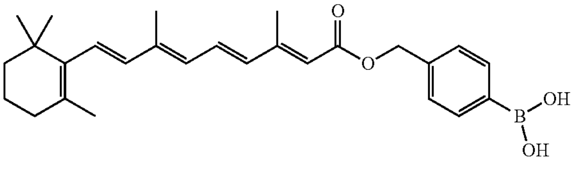

The RABA is in a form in which a boron functional group is bound to a terminal of retinoic acid.

Since the boron functional group in RABA is slightly polar and hydrophilic, RABA becomes amphipathic by the bonding of the boron functional group. Amphipathic RABA undergoes self-assembly in an aqueous solution to form nanoparticles. Moreover, RABA has structural flexibility. Therefore, RABA undergoes self-assembly in an antisolvent, typically in water, to form stable colloidal nanoparticles. Therefore, the present invention provides nanoparticles formed by self-assembly of RABA.

The nanoparticles have both the efficacy of ‘anticancer’ and the efficacy of ‘tumor targeting.’ Therefore, the present invention provides the nanoparticles as ‘tumor-targeting anti-cancer nanoparticles.’

Figure 1:
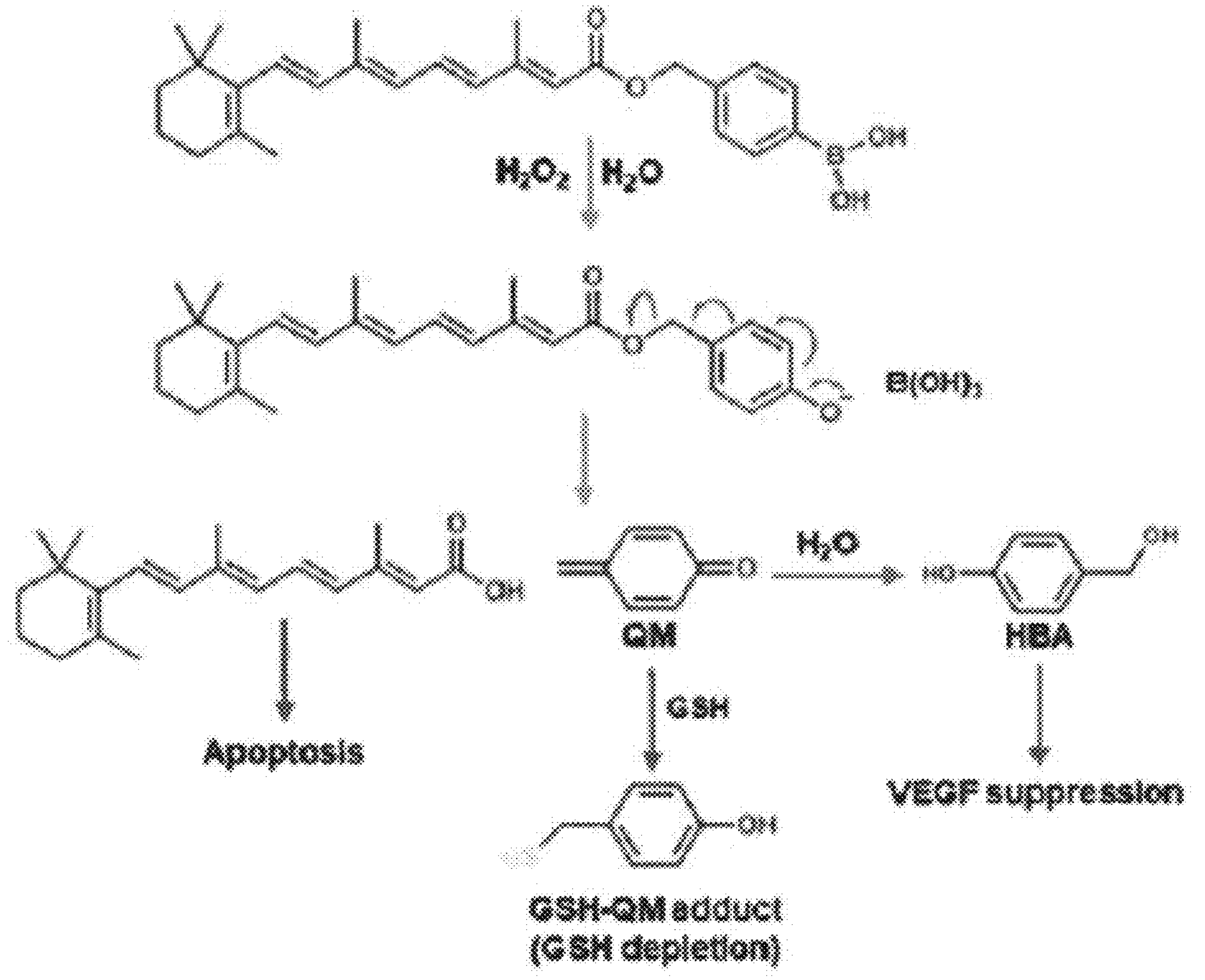
FIG. 1 shows an anticancer action mechanism of RABA nanoparticles of the present invention.

First, the efficacy of ‘anticancer’ is explained from the anticancer action mechanism shown in FIG. 1. In other words, when the boron functional group in the nanoparticle reacts with hydrogen peroxide, which exists at a high concentration in cancer cells, a quinone methide (QM) intermediate is formed, and at the same time, retinoic acid (RA) is released. The QM exhibits an anticancer effect that kills cancer cells by amplifying intracellular oxidative stress by removing cellular antioxidant glutathione (GSH). In addition, the released RA induces cancer cell death, that is, apoptosis, thereby causing cancer cell death. Therefore, RABA of the present invention exhibits excellent anticancer efficacy from the synergistic effect of QM, which depletes GSH, and RA, which induces apoptosis. Furthermore, QM reacts with nucleophilic water to produce hydroxybenzyl alcohol (HBA). In other words, QM competitively reacts with GSH and water to produce HBA. The HAB produced at this time inhibits angiogenesis by inhibiting vascular endothelial growth factor (VEGF), which promotes angiogenesis, thereby brining an effect of inhibiting cancer metastasis.

RABA forms nanoparticles in the manner of self-assembly in an aqueous solution due to its amphiphilic nature, so the preparation method for the RABA nanoparticles of the present invention is very simple. In addition, there is no need to add separate ingredients such as excipients in forming nanoparticles from RABA. Therefore, the nanoparticles produced at this time may be composed of 100% by weight of RABA. This means that a drug can be prepared to have a content of 100% by weight without the need to add other ingredients such as excipients in the particles. Therefore, the nanoparticles of the present invention can maximize pharmacological effects. In other words, a maximum effect can be exhibited with a minimal use.

Next, for the efficacy of ‘tumor targeting,’ the present invention provides the nanoparticles in a surface-modified state by coating the nanoparticle surface with γ-polyglutamic acid (γPGA). Therefore, the surface of the nanoparticles of the present invention preferably has a form coated with γPGA. γPGA can bind to gamma glutamyl transferase (GGT), which is overexpressed in the surface membrane of various tumor cells, and nanoparticles that are surface-modified with γPGA specifically target GGT-overexpressed cancer cells. Then, as described above, when RA and QM are released by the triggering by $H_2O_2$, an anticancer effect is exhibited.

In the present invention, dopamine is first used as an anchor for the nanoparticle surface modification. Dopamine has a positive charge and a strong binding ability of catechol. Dopamine is adsorbed to the RABA nanoparticle surface as a complex is formed between the catechol and amine groups of dopamine and boronic acid. Then, γPGA is adsorbed to the dopamine-adsorbed surface of RABA due to electrostatic attraction between a carboxylate and an amine.

Figure 2:
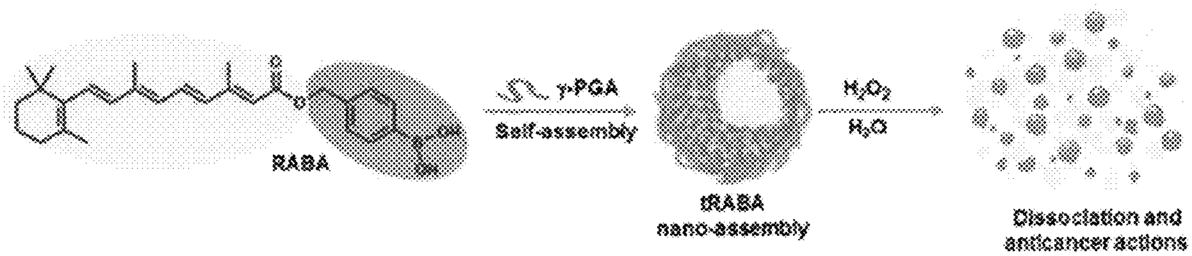
FIG. 2 a preparation and decomposition process of RABA nanoparticles of the present invention.

FIG. 2 briefly shows the process of preparing and decomposing the nanoparticles of the present invention. First, nanoparticles are prepared through self-assembly of RABA, and at this time, γ-polyglutamic acid is added to coat the surface of the formed nanoparticles. ‘tRABA’ prepared in this manner is decomposed in the presence of hydrogen peroxide and water to exhibit anticancer activity through the mechanism shown in FIG. 1.

The present invention provides an anticancer drug composition including the nanoparticles as an active ingredient. The composition may include additional drugs, adjuvants, or excipients for anticancer effects in addition to the nanoparticles of the present invention.

Hereinafter, the present invention will be described in more detail through examples. However, the present invention should not be considered limited thereto.

MODES OF INVENTION

Examples

1. Preparation of RABA

RABA was prepared in the following order.

(a)

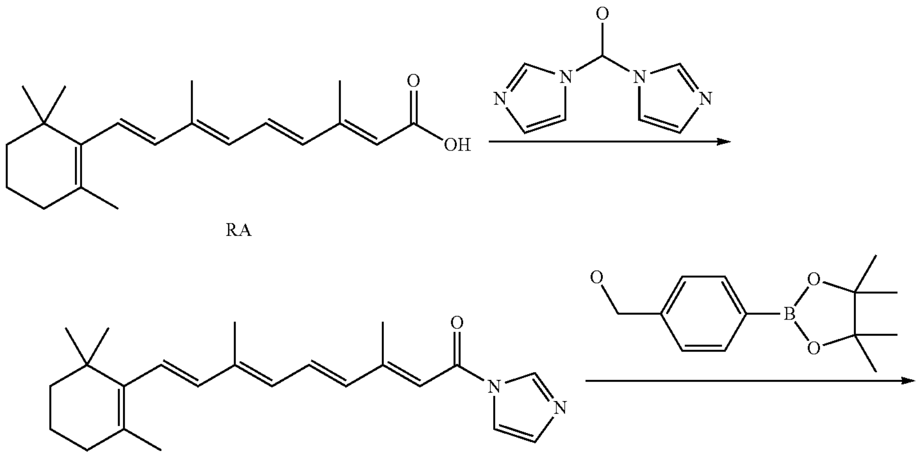

RA

1

-continued

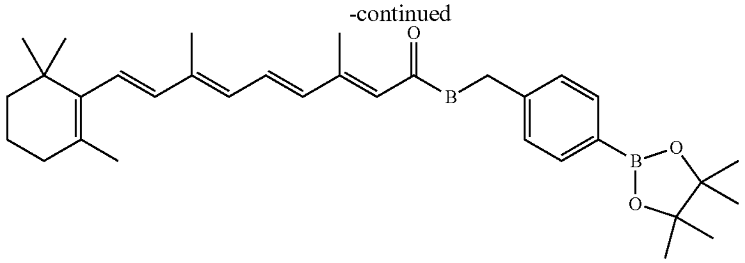

2

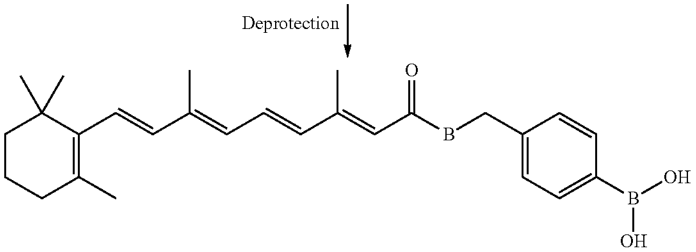

RABA

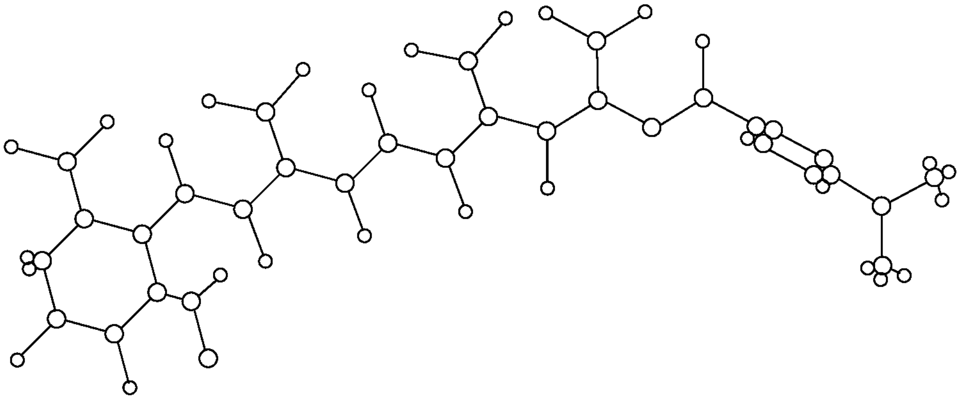

First, Compound 1 was synthesized through a reaction of RA and carbonyldiimidazole, and Compound 1 was subject to a reaction with 4-(hydroxymethyl)phenylboronic acid pinacol ester to prepare Compound 2. Next, a cyclic boronate ester of Compound 2 was removed to obtain RABA.

Figure 3A:
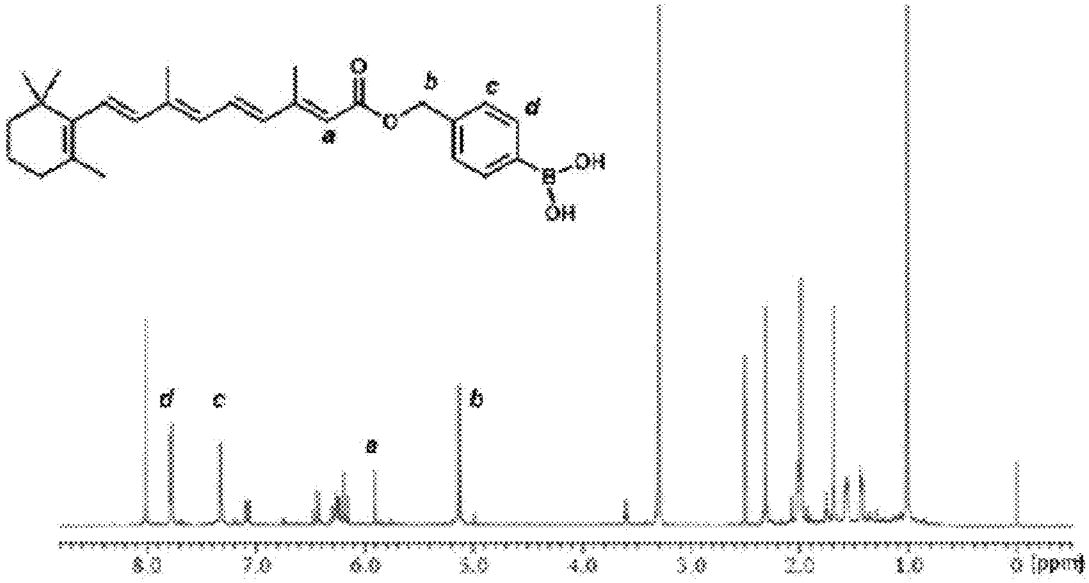
FIG. 3A shows $^1H$ NMR data of RABA prepared in an embodiment.
Figure 3B:
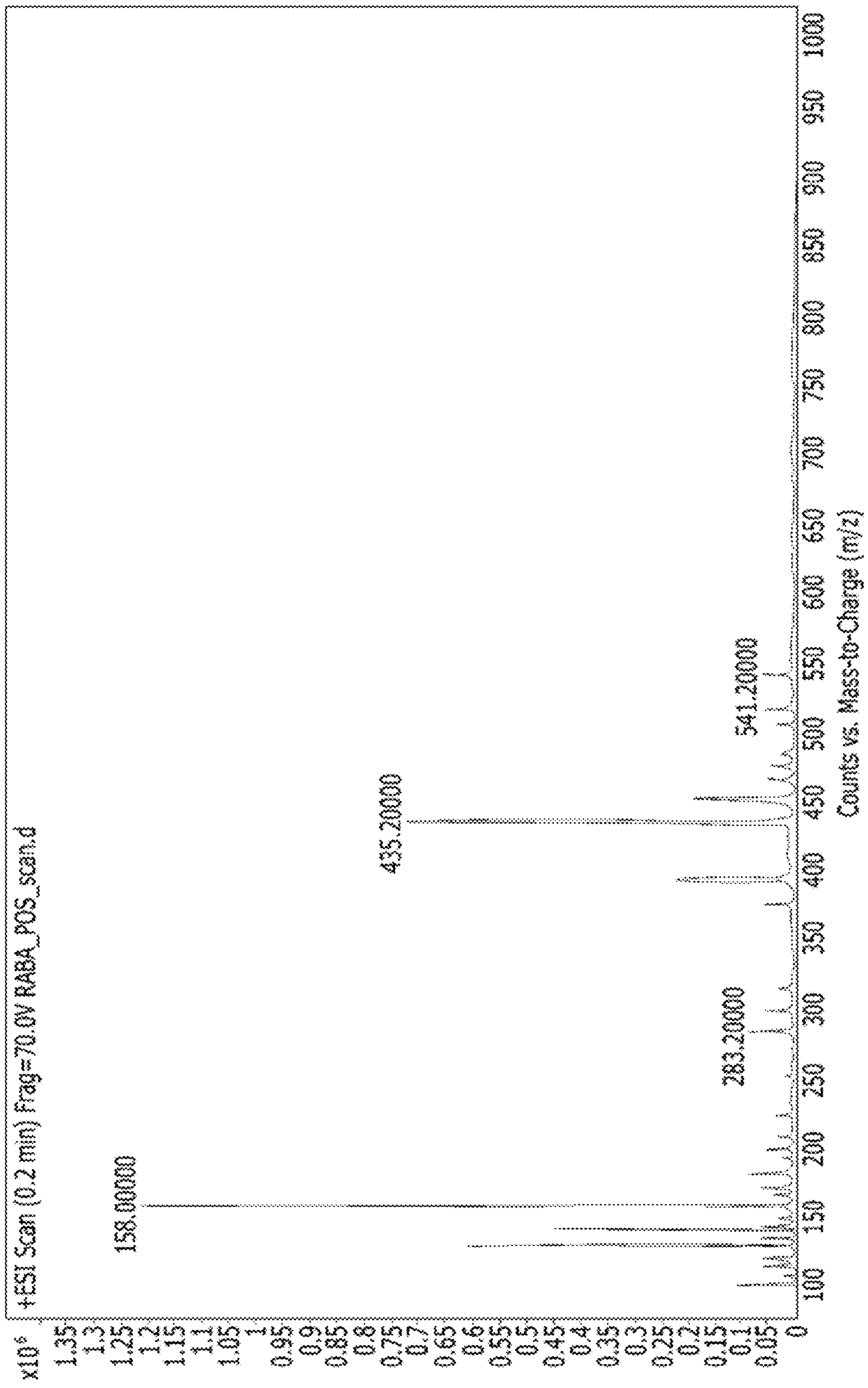
FIG. 3B shows the results of mass spectrometer measurement of RABA.

FIG. 3A shows the $^1H$ NMR data of the prepared RABA. The 5.1 ppm peak corresponds to methylene between an ester and a benzene ring. In addition, FIG. 3B shows the results of mass spectrometer measurement of the molecular weight of the RABA. The molecular weight of RABA was measured to be 435.20 m/z [M].

2. Evaluation of Reactivity of RABA in the Presence of $H_2O_2$

Figure 4:
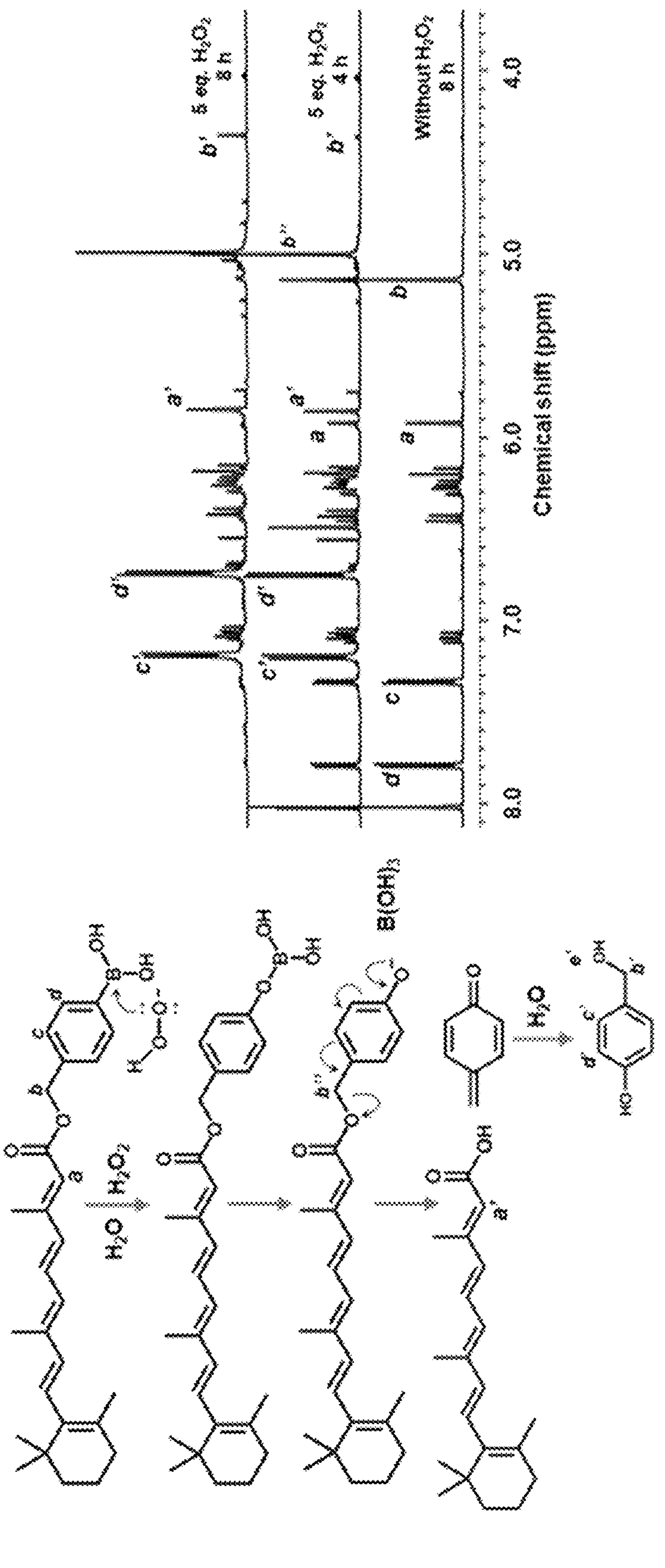
FIG. 4 shows $^1H$ NMR data after incubation of RABA in an $H_2O_2$ solution.

To evaluate the reactivity of the prepared RABA in the presence of $H_2O_2$, $^1H$ NMR of the RABA was taken after incubation in a 5 mM $H_2O_2$ solution. The results are shown in FIG. 4.

According to the results, a shift of the peak due to the release of HBA was observed in the $H_2O_2$-treated RABA. The peaks at 7.3 and 7.8 ppm corresponding to aromatic protons disappeared, and new peaks at 6.8 and 7.1 ppm appeared. The peaks corresponding to benzylic proton were shifted from 5.1 ppm to 5.0 ppm. On the other hand, there was no peak shift in the RABA incubated in water without $H_2O_2$. These results show that RABA exists in a stable form in water but may release QM in the presence of $H_2O_2$.

3. Self-Assembly of RABA

Figure 5A:
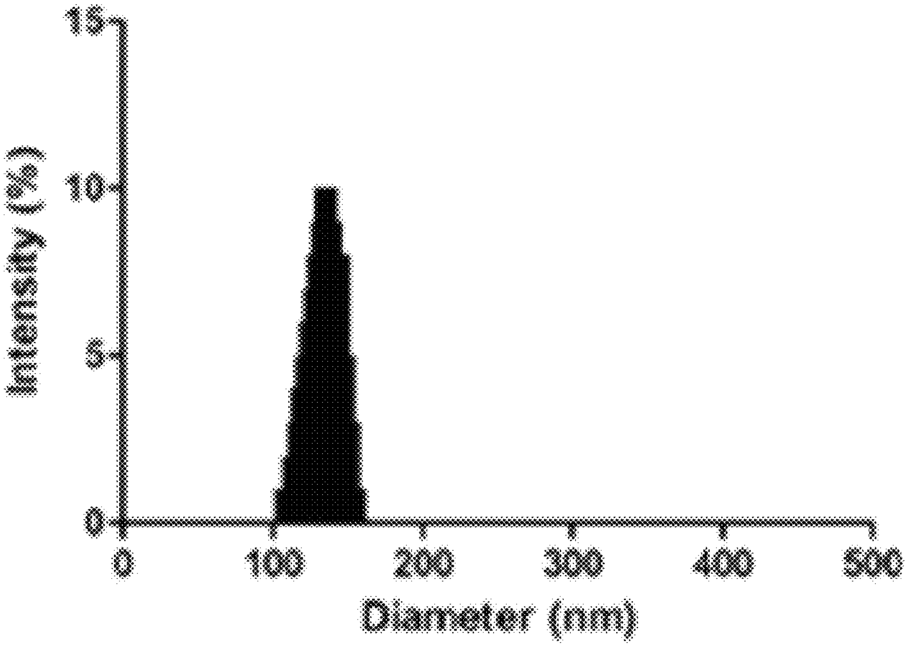
FIG. 5A shows a size distribution of RABA nanoparticles.

RABA dissolved in tetrahydrofuran (THF) was added to water while stirring. During dilution in water, strong light scattering occurred due to the Tyndall phenomenon. This showed that the nanoparticles were being formed well. The results of measuring the size of the formed nanoparticles are shown in FIG. 5A. The mean hydrodynamic diameter was measured to be ~120 nm.

Figure 5B:
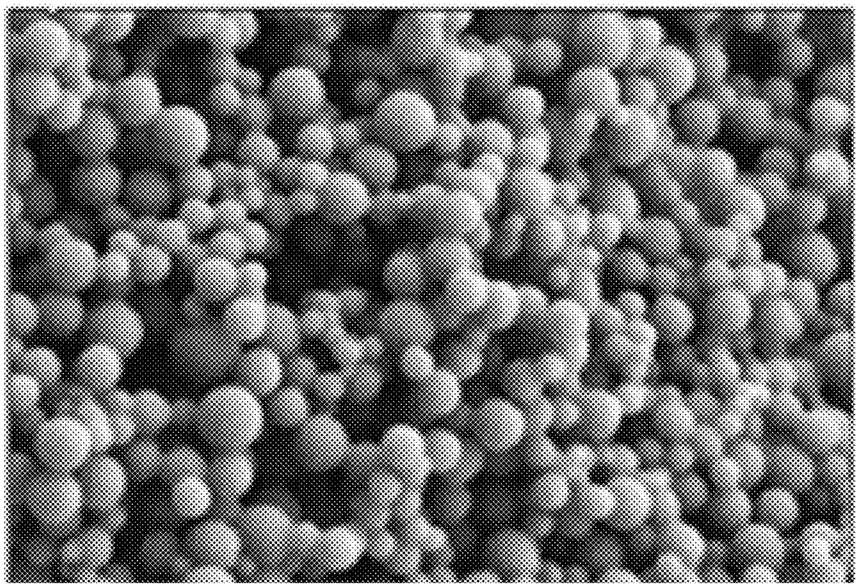
FIG. 5B shows a SEM photograph of RABA nanoparticles.
Figure 5C:
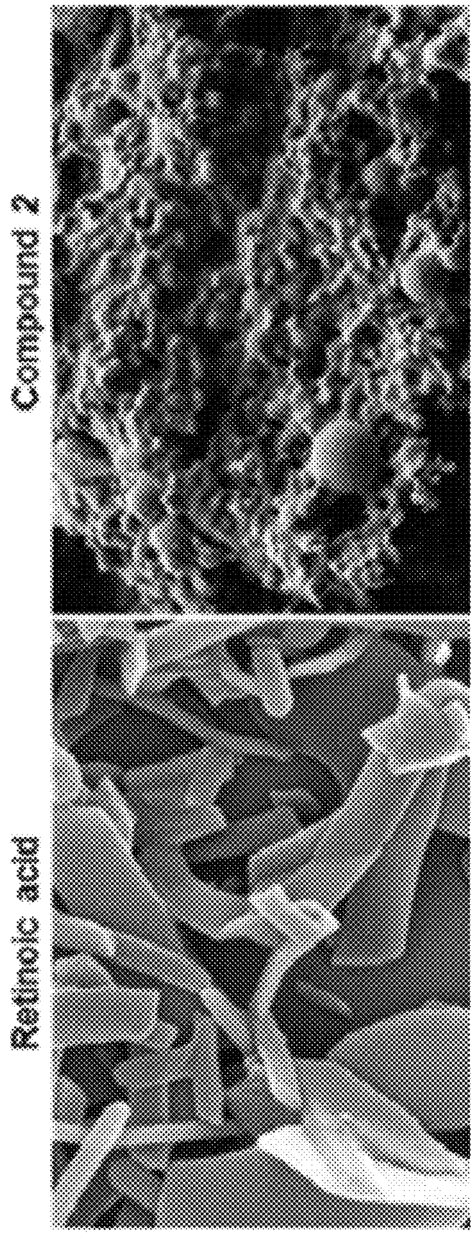

In addition, FIG. 5B shows a SEM photograph of the self-assembled RABA nanoparticles. It was confirmed that the nanoparticles existed in a spherical colloidal state. In addition, an experiment was performed to confirm self-assembly of Compound 2, which is produced during the preparation process of RA and RABA. The results are shown in FIG. 5C. According the results, it was confirmed that RA and Compound 2 failed to undergo self-assembly and large precipitates of an irregular shape were formed instead.

In other words, it can be seen that only RABA, which is amphipathic and structurally flexible, may form nanoparticles with a stable structure and shape through self-assembly.

4. Preparation of γPGA-Coated RABA (tRABA)

After dopamine was adsorbed on RABA, γPGA was adsorbed on the surface of RABA on which dopamine was adsorbed. First, water in which RABA nanoparticles were dispersed and an dopamine aqueous solution were mixed, the resulting mixture was stirred for 1 hour, and nanoparticles on which dopamine was adsorbed were separated through centrifugation. Next, the nanoparticles on which dopamine was adsorbed were dispersed in water and mixed with a γPGA aqueous solution, and the resulting mixture was stirred for 1 hour. Then, γPGA-coated RABA nanoparticles were separated through centrifugation.

Figure 6A:
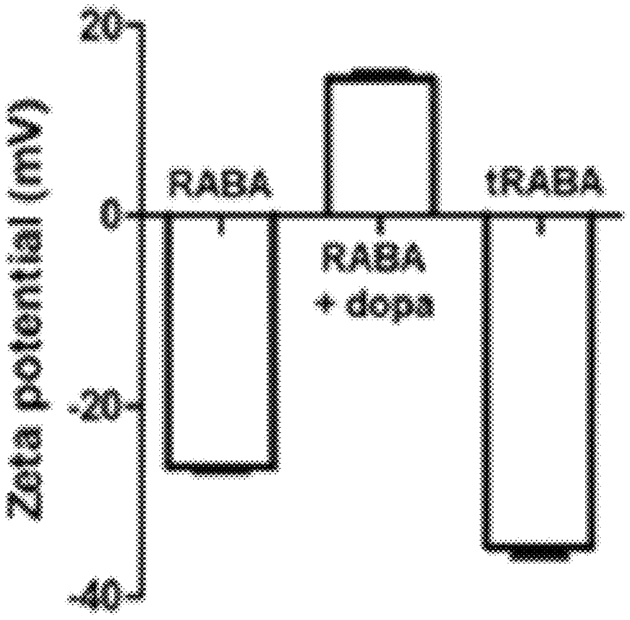
FIG. 6A shows zeta potential of RABA, RABA+dopamine, and tRABA at pH 7.

The zeta potential of the prepared tRABA at pH 7 was measured. The results are shown in FIG. 6A. The negative charge of tRABA is thought to be due to the numerous carboxylate groups of PGA.

Figure 6B:
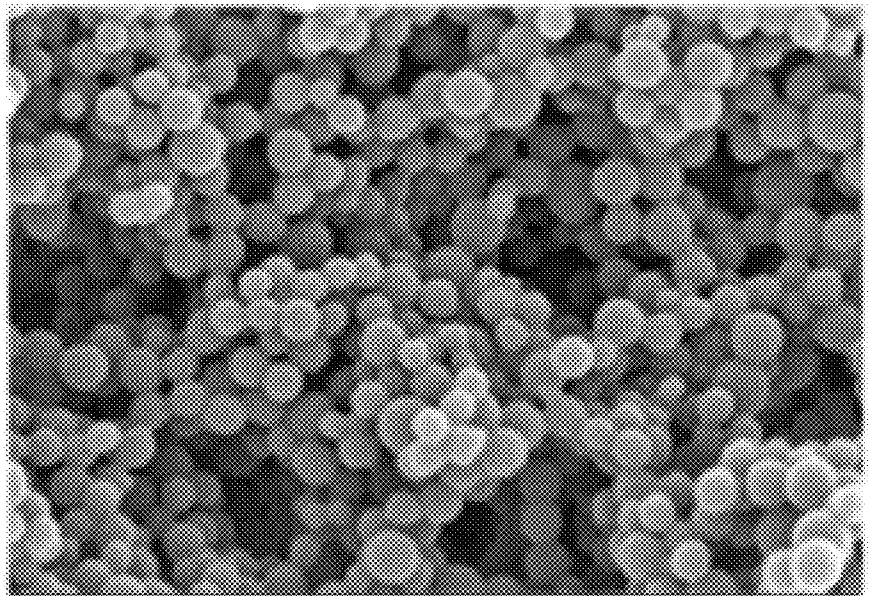
FIG. 6B shows a SEM photograph of tRABA.
Figure 6C:
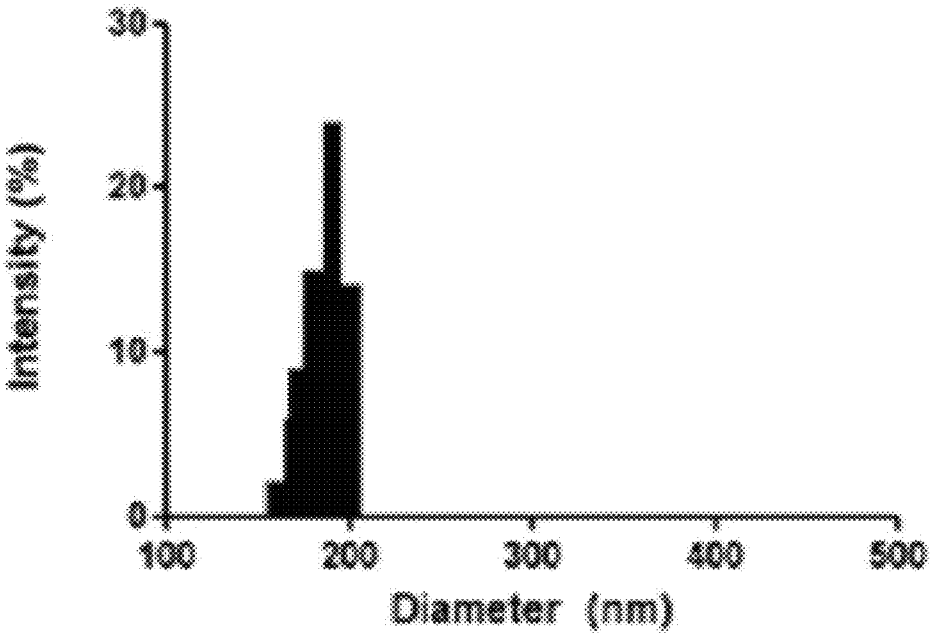
FIG. 6C shows a size distribution of tRABA.

FIGS. 6B and 6C show the SEM images of tRABA and the results of particle size measurement. tRABA maintained its spherical colloidal state as in RABA, and the mean hydrodynamic diameter was measured to be ~160 nm, confirming that the particle size had slightly increased as tRABA became tRABA.

Figure 6D:
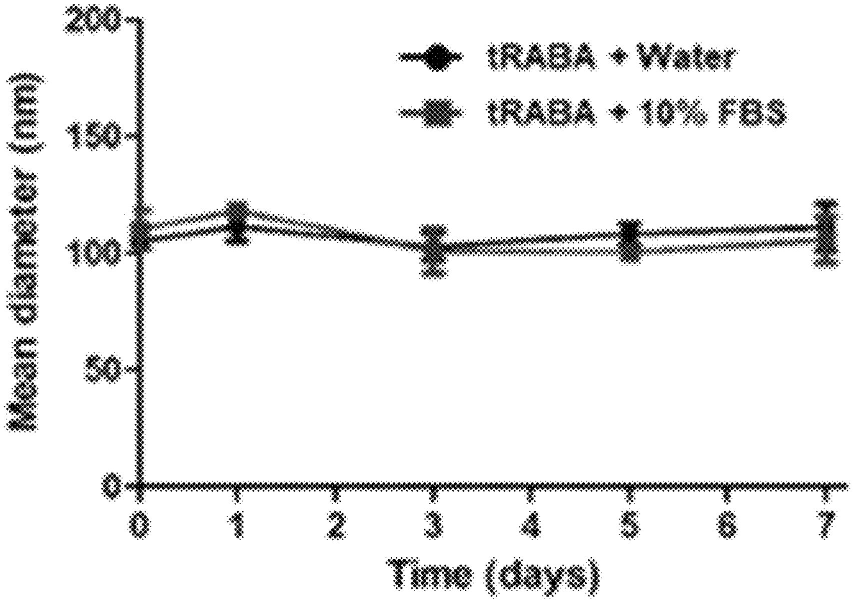
FIG. 6D shows size change of tRABA when stored in PBS including water and fetal bovine serum (10 wt %).
Figure 6E:
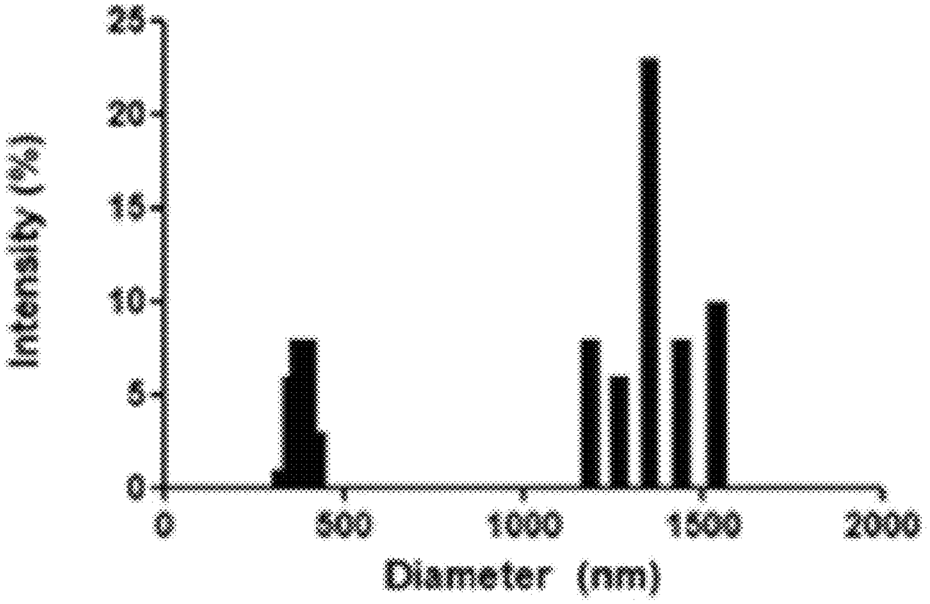
FIG. 6E is a size distribution of tRABA after incubation in PBS including $H_2O_2$ (1 mM).

Next, tRABA was added to PBS including fetal bovine serum (10 wt %) and incubated for 7 days to observe the particle size. The results are shown in FIG. 6D. According to the results, it can be seen that the tRBAB maintains excellent colloidal stability in a physiological solution. On the other hand, according to FIG. 6E, which shows the result of incubating in PBS including $H_2O_2$ (1 mM) for 5 hours, the tRABA lost its structural binding and showed a significant change in the particle size and the size distribution. In other words, it was confirmed that tRABA is decomposed in the presence of $H_2O_2$ as shown in FIG. 2.

Figure 6F:
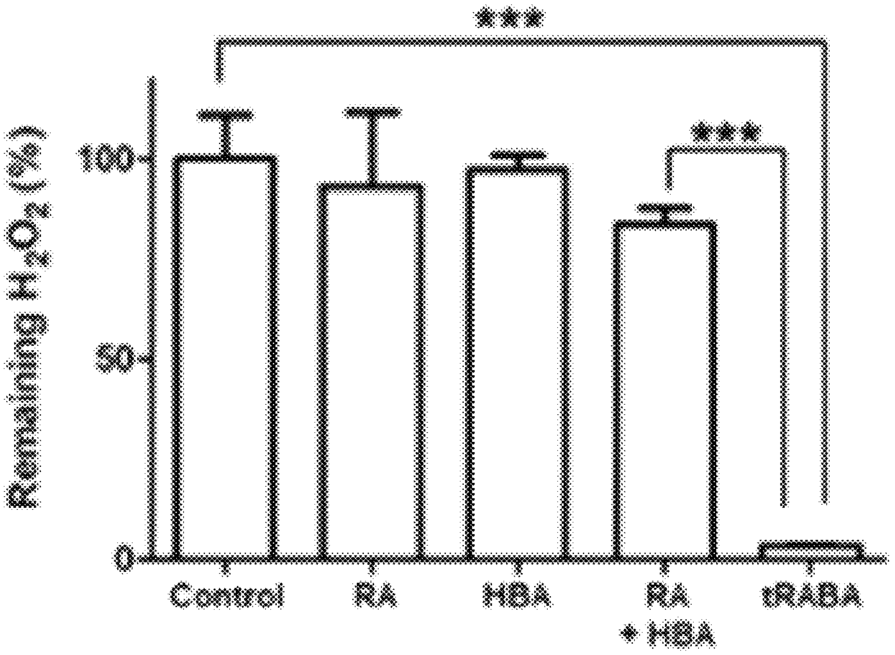
FIG. 6F compares $H_2O_2$ depletion by RA, HBA, RA+HBA, and tRABA.

Next, $H_2O_2$ depletion by tRABA was evaluated. This is because tRABA, like RABA, is predicted to deplete $H_2O_2$ through deboronation of aryl boronic acid in the presence of $H_2O_2$. $H_2O_2$ depletion was evaluated by comparing RA, HBA, and RA+HBA. RA (65 mg/mL), HBA (28 mg/mL), RA (65 mg/mL)+HBA (28 mg/mL), and tRABA (100 mg/mL) were each added to 1 mL of 100 mM $H_2O_2$ aqueous solution and stir for 1 hour. After mixing a tetrahydrofuran solution in which diphenine peroxalate and rubulin were dissolved with the $H_2O_2$ solution, the concentration of hydrogen peroxide was quantified by a chemimulinescence principle (peroxalate chemimulinescence) using a luminometer (FB12 Berthold Detection System) (Jung et al. Molecularly engineered theranostic nanoparticles for thrombosed vessels: H2O2-activatable contrast-enhanced photoacoustic imaging and antithrombotic therapy, ACS Nano, 2018, 12 (1), 392). The results are shown in FIG. 6F. According to the results, it can be confirmed that in the case of tRABA, the amount of $H_2O_2$ was significantly reduced. From this, it could be seen that tRABA also reacts by depleting $H_2O_2$.

5. Evaluation of Cellular Uptake and Tumor Penetration of tRABA Nanoparticles

Figure 7A:
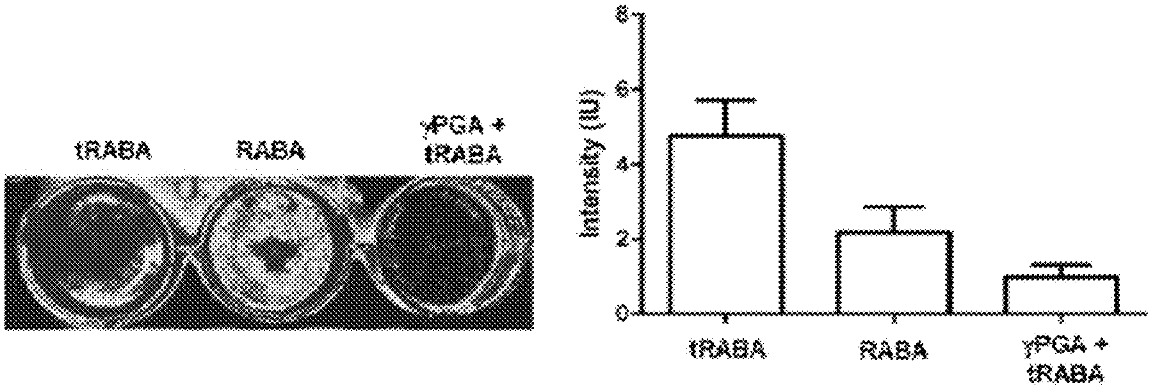
FIG. 7A shows a fluorescence image obtained 1 hour after adding tRABA nanoparticles loaded with fluorescent Nile Red to GGT immobilized on a 96-well microplate.

The fluorescence image shown FIG. 7A was obtained 1 hour after adding tRABA nanoparticles loaded with fluorescent Nile Red to GGT immobilized on a 96-well microplate. The nanoparticles treated with tRABA showed higher fluorescence intensity compared to RABA. This shows that tRABA binds to GGT much better than RABA. On the other hand, when tRABA was added after pretreatment with γPGA, the binding of tRABA to GGT was disrupted by γPGA, and so fluorescence did not appear. This ultimately shows that the binding of tRABA to GGT is achieved by γPGA on the surface.

Figure 7B:
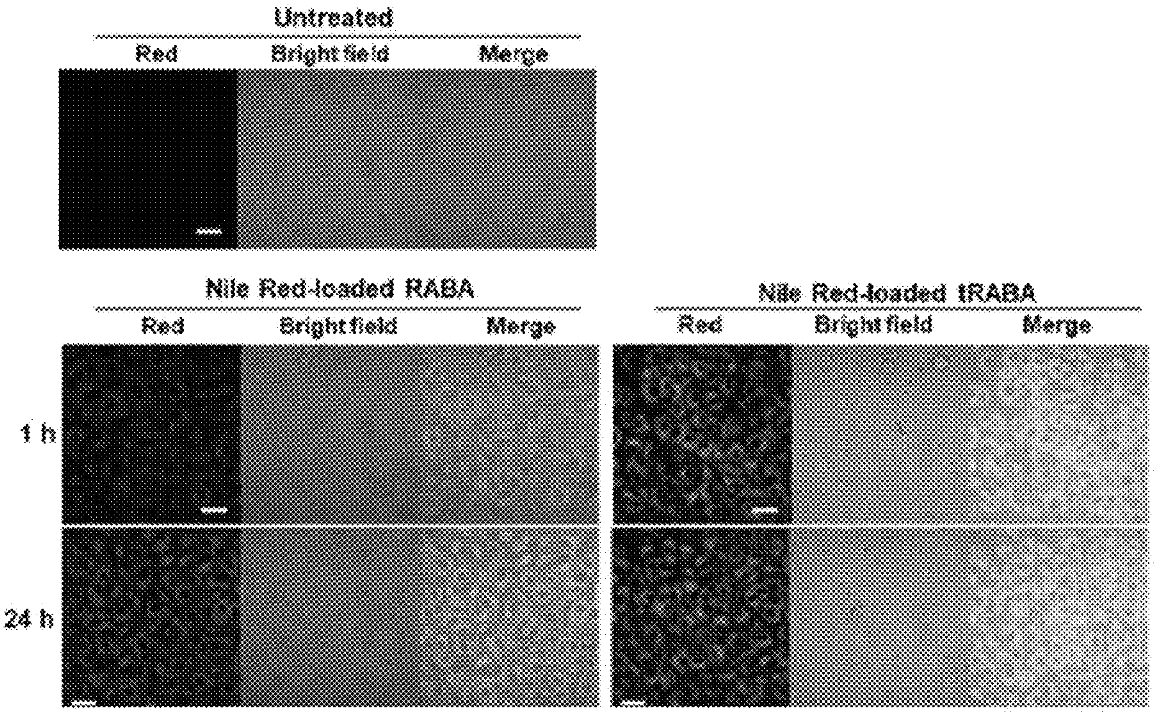
FIG. 7B shows a fluorescence image obtained after incubating tRABA nanoparticles loaded with fluorescent Nile Red in SW620 cells.

Next, to evaluate cellular uptake and internalization of tRABA, fluorescence images were obtained after incubating SW620 cells with Nile Red-loaded tRABA nanoparticles for 1 hour and 24 hours. The results are shown in FIG. 7B. According to the results, it can be seen that over time, red fluorescence spread widely in the cytoplasm and thus the signal intensity increased. Cells treated with tRABA exhibited much higher fluorescence intensity than those treated with RABA. This shows that tRABA entered into the cells faster than RABA by GGT-dependent endocytosis.

Figure 7C:
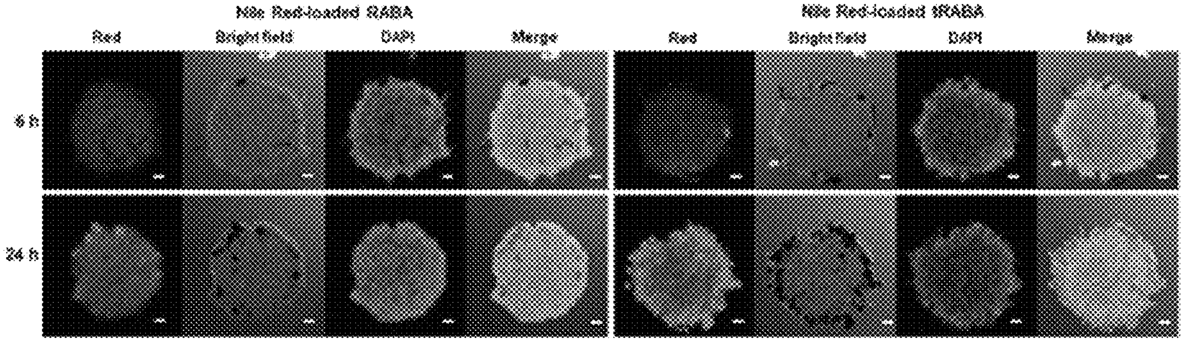
FIG. 7C shows a fluorescence image of multicellular spheroids obtained after incubating with fluorescent tRABA nanoparticles and fluorescent RABA nanoparticles for 6 hours and 24 hours, respectively.

Next, SW620 multicellular spheroids were used to evaluate the tumor penetration of Nile Red-loaded tRABA nanoparticles. FIG. 7C shows fluorescence images of multicellular spheroids obtained after incubating with fluorescent tRABA nanoparticles and fluorescent RABA nanoparticles for 6 hours and 24 hours, respectively. According to the results, weak fluorescence appeared from both spheroids after 6 hours. However, after 24 hours, tRABA-treated spheroids showed much higher fluorescence intensity than RABA-treated spheroids. This means that tRABA penetrated much deeper into the spheroids than RABA. From this, it could be confirmed that tRABA has excellent tumor penetration.

Figure 8A:
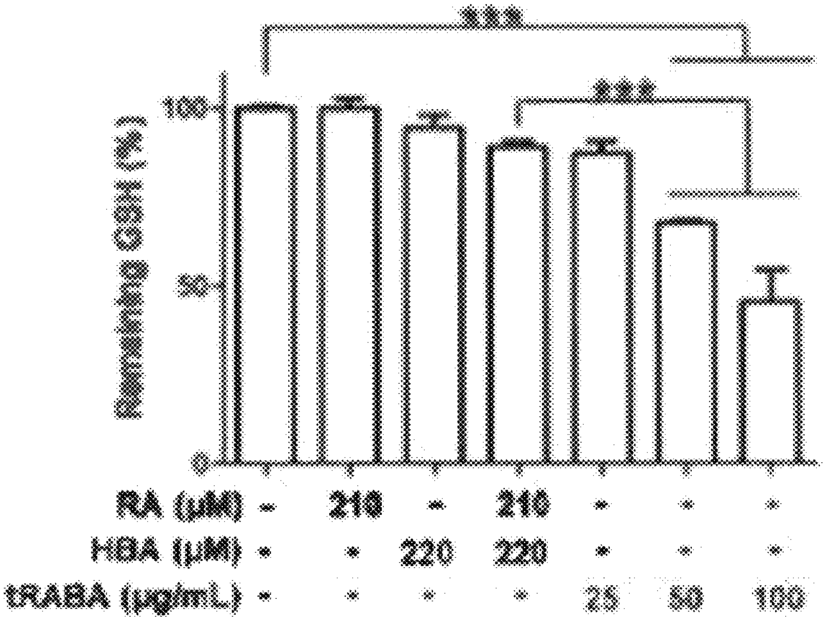
FIG. 8A shows comparison of intracellular GSH levels in A549 cells treated with RA, HBA, RA+HBA, and tRABA.

6. Evaluation of Anticancer Activity of tRABA tRABA releases QM, which depletes GSH in the presence of $H_2O_2$, and QM competitively reacts with GSH and water to produce HBA. Therefore, an experiment was conducted to measure intracellular GSH levels in A549 cells treated with tRABA. The results are shown in FIG. 8A. According to the results, cells treated with RA (210 mM) and HBA (210 mM) alone or together had no effect on the GSH levels. On the other hand, in the cells treated with tRABA, a change in the GSH levels was observed in a concentration-dependent manner. This is because the arylboronic acid moiety of tRABA was decomposed to generate QM, which combined with GSH, thereby depleting the intracellular GSH.

Figure 8B:
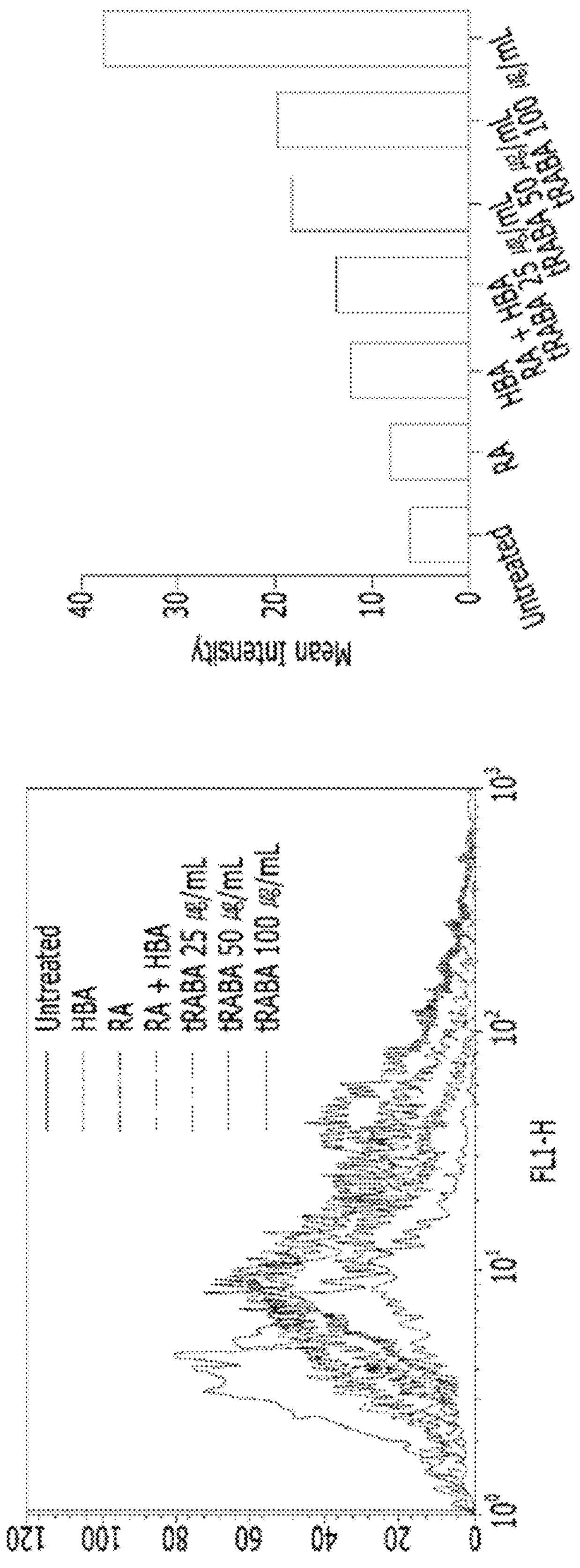
FIG. 8B shows comparison of ROS levels in cancer cells treated with RA, HBA, RA+HBA, and tRABA.

Next, to evaluate the effect of tRABA on the level of reactive oxygen species (ROS) in cancer cells, an experiment was performed by using DCFH-DA as a probe for ROS. The results are shown in FIG. 8B. According to the results, it can be seen that RA induced the production of ROS in the cells to some extent and tRABA also induced the production of ROS in a concentration-dependent manner. In particular, 100 mg/mL of tRABA induced significantly more ROS production compared to the equivalent level of RA (210 mM). This suggests that even when all QM produced from the deboronization at tRABA, which is triggered by $H_2O_2$, fail to react with GSH due to competitive reaction with the nucleophilic water, there is a cooperative production of ROS by QM, which depletes RA and GSH.

Figure 8C:
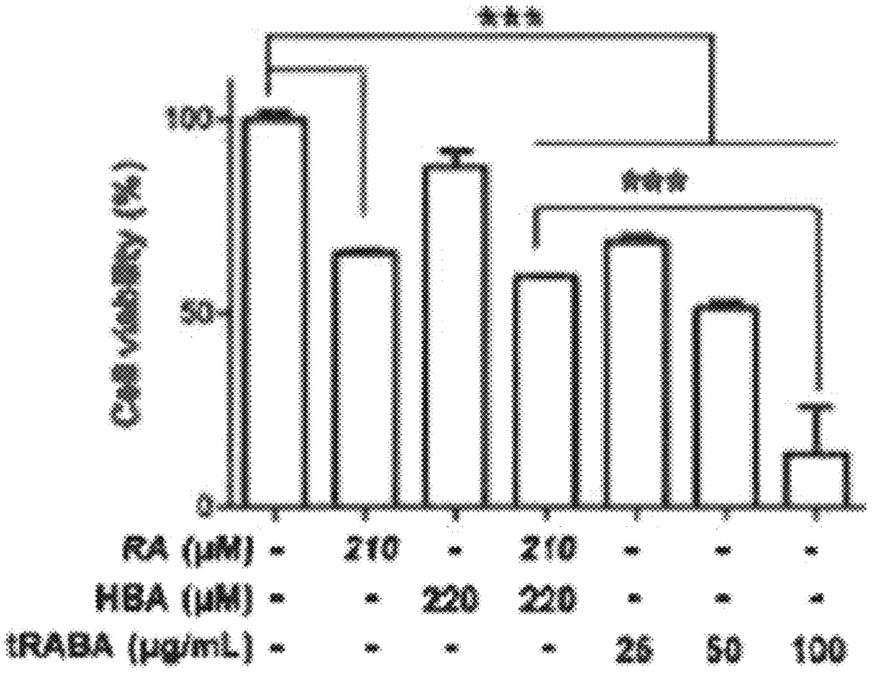
FIG. 8C shows comparison of cell survival rates 24 hours after treating A549 cells with RA, HBA, and tRABA.

Next, to evaluate the cytotoxicity of tRABA, a 3-(4,5-dimethylthiazol-2-yl)-2,5-diphenyltetrazolium bromide (MTT)) analysis was performed. The cell survival rate was measured 24 hours after A549 cells were treated with RA, HBA, and tRABA, and the results are shown in FIG. 8C. In the cells treated with RA (210 mM), the cell survival rate decreased due to the apoptosis-inducing ability of RA. The HBA (220 mM)-treated cells exhibited negligible cytotoxicity. As anticipated from the cooperative production of ROS in the previous experiment, the cells treated with 100 mg/mL tRABA showed very high cytotoxicity compared to the equivalent combination of RA (210 mM) and HBA (220 mM).

Figure 8D:
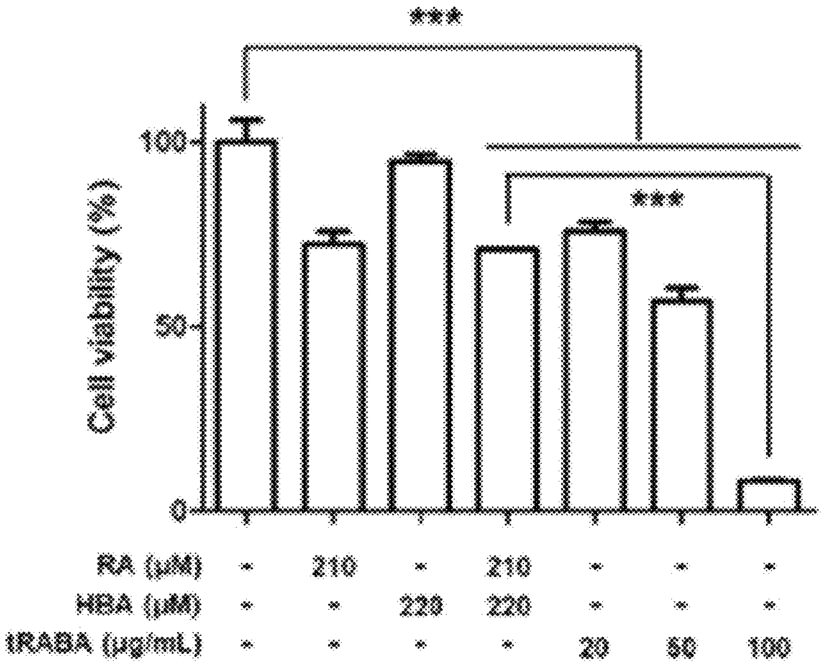
FIG. 8D shows comparison of cell survival rates 24 hours after treating SW620 cells with RA, HBA, and tRABA.

Next, cytotoxicity on SW620 cells was tested, and the results are shown in FIG. 8D. From the results, it could be seen that tRABA has a synergistic anticancer effect by releasing RA, which produces ROS, and QM, which depletes GSH.

Figure 8E:
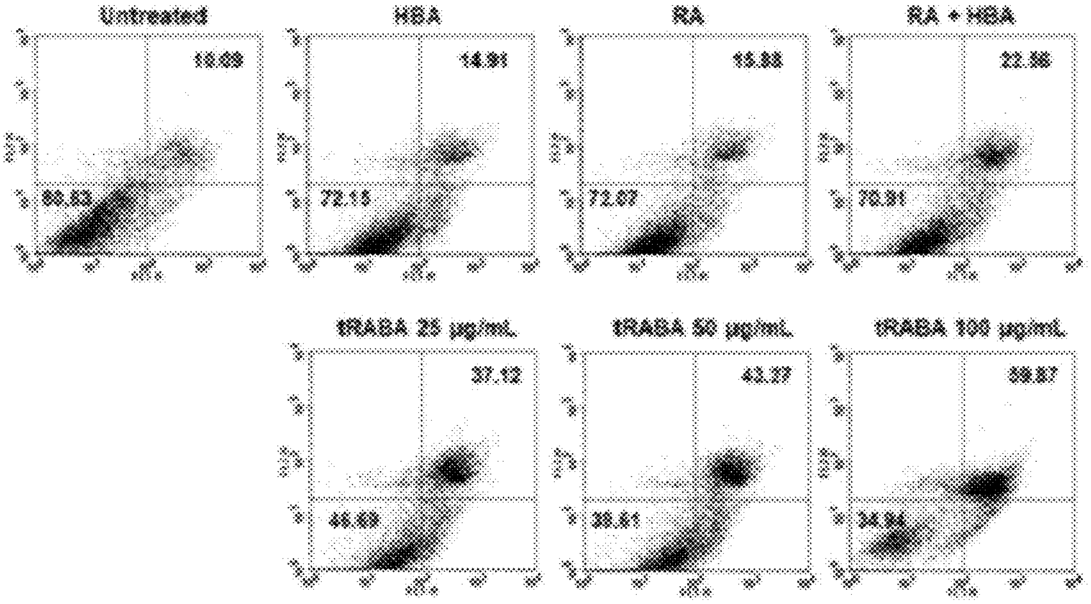
FIG. 8E shows comparison of apoptosis inducing ability of RA, HBA, RA+HBA, and tRABA.

Next, to evaluate the ability of tRABA to induce apoptosis, a flow cytometric analysis was performed using Annexin V-FITC as an apoptosis marker and propidium iodide as a cell viability marker. Apoptotic cells induced by RA are represented by the increased distribution in the upper right quadrant of FIG. 8E. From this, it could be confirmed that tRABA induces concentration-dependent apoptosis much more effectively than the equivalent levels of RA and HBA.

Figure 8F:
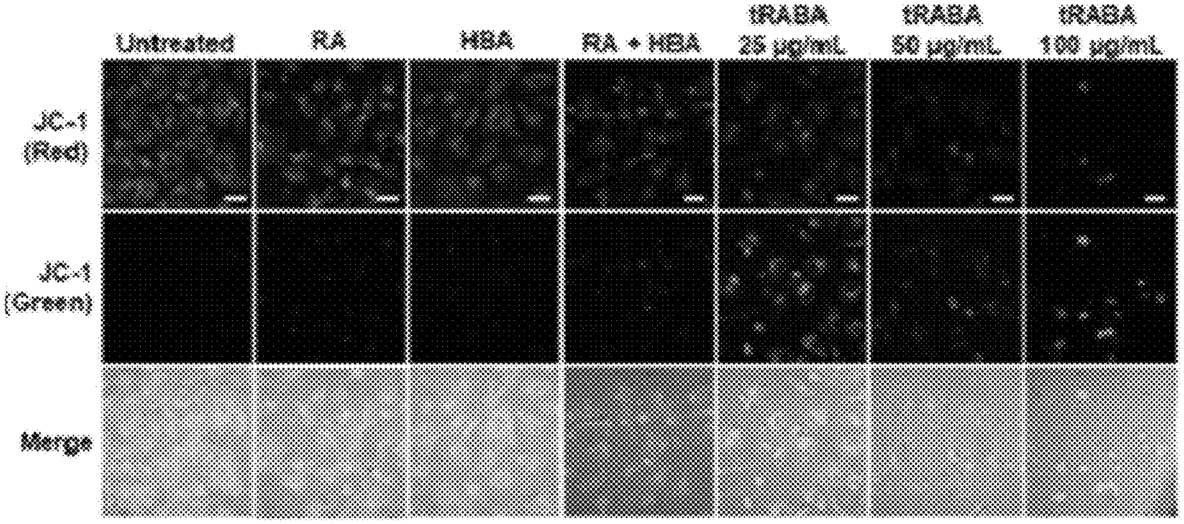
FIG. 8F shows the results of confocal laser scanning microscopy using mitochondrial membrane potential probe JC-1 die for RA, HBA, RA+HBA, and tRABA.

Next, since it is known that mitochondria play an important role in activating apoptosis and that one of the conserved aspects of apoptosis is mitochondrial collapse, confocal laser scanning microscopy was performed using JC-1 die as a mitochondrial membrane potential probe. The results are shown in FIG. 8F. From the increased green/red fluorescence intensity ratio, it can be seen that tRABA caused a significant decrease in the membrane potential. From this, it can be seen that tRABA caused more mitochondrial damage compared to the equivalent levels of RA and HBA, indicating that GSH depletion enables the anticancer activity of RA that induces apoptosis.

Figure 8G:
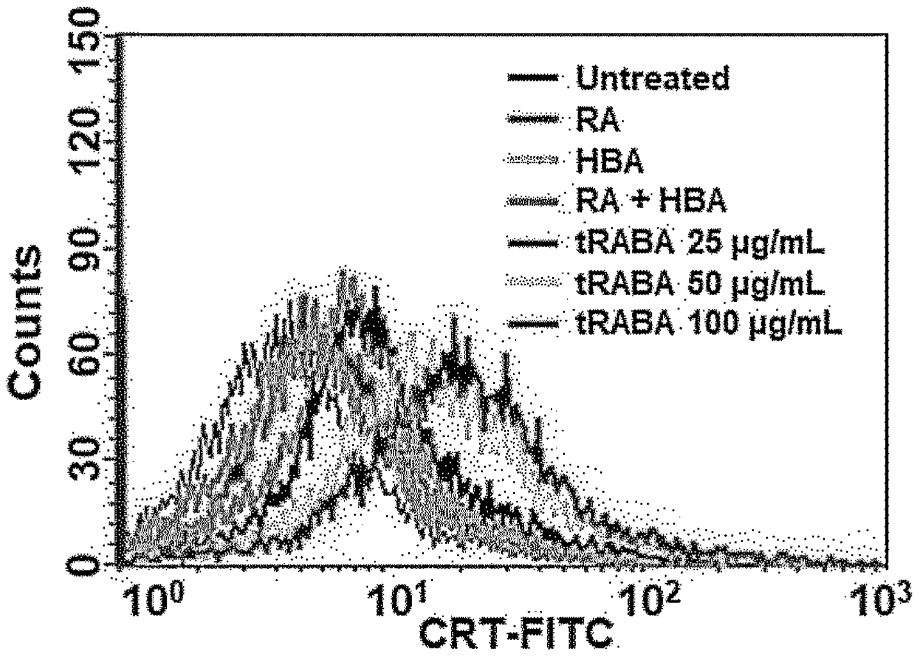
FIG. 8G shows the results of an analysis of CRT expression levels in cells treated with RA, HBA, RA+HBA, and tRABA.

Next, since immunogenic apoptosis enhances immunogenicity and anticancer effects by releasing damage-associated molecular pattern (DAMP) substances during the cell dying process, an experiment was performed to confirm whether tRABA nanoparticles induce immunogenic cell death to improve immunogenicity. First, the expression levels of DAMPs such as calreticulin (CRT) and high mobility group box 1 (HMGB1) were confirmed as endoplasmic reticulum (ER) stress markers. Since it is known that CRT is present in the perinuclear endoplasmic reticulum but moves to the cell membrane during early apoptotic stages, and CRT on the cell membrane promotes phagocytosis by dendritic cells and induce immunogenicity, a flow cytometric analysis was performed to confirm the CRT level in A549 cells after tRABA treatment. As shown in FIG. 8G, it was confirmed that RA and HBA had almost no effect, while tRABA nanoparticles significantly increased the level of CRT.

Figure 8H:
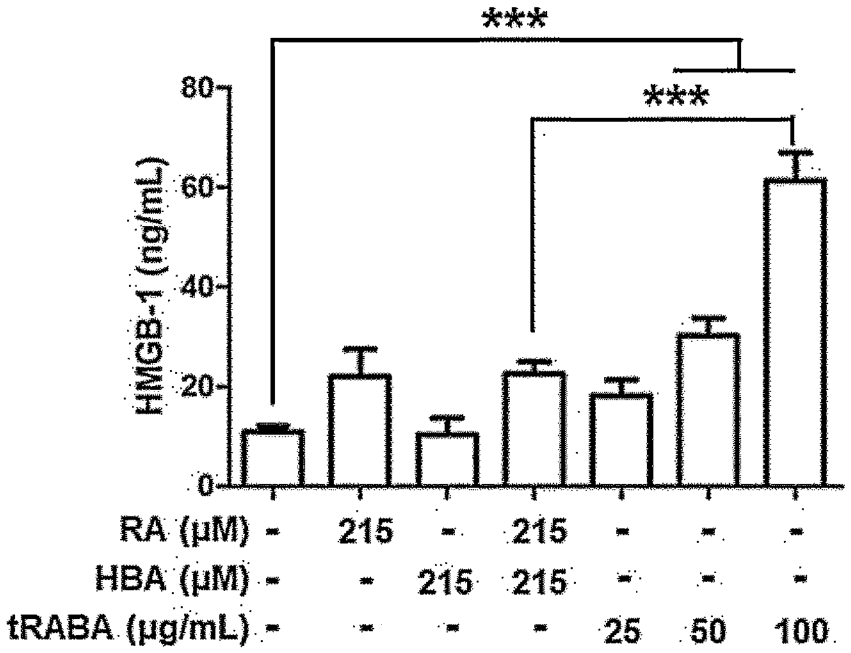
FIG. 8H shows comparison of levels of HMGB1 released from A549 cells treated with RA, HBA, and tRABA.'

Next, since it is known that HMGB-1 is a nuclear protein that binds to DNA and is triggered by an apoptosis inducer and that in the late stage of apoptosis, cells are destroyed and HMGB-1 is released into the tumor microenvironment to induce dendritic cell maturation and antigen presentation, an experiment was performed to confirm the effect of tRABA nanoparticles on HMGB-1 release. As shown in FIG. 8H, it was confirmed that HBA did not affect the level of HMGB-1, while RA significantly increased the level of HMGB-1, and that tRABA nanoparticles increased the level of HMGB-1 in a concentration-dependent manner. Through this, it could be seen that tRABA nanoparticles increase ER stress to release CRT and HMGB-1 and induce immunogenic cancer cell death.

7. Therapeutic Effect of tRABA on Tumor Animal Models

Figure 9A:
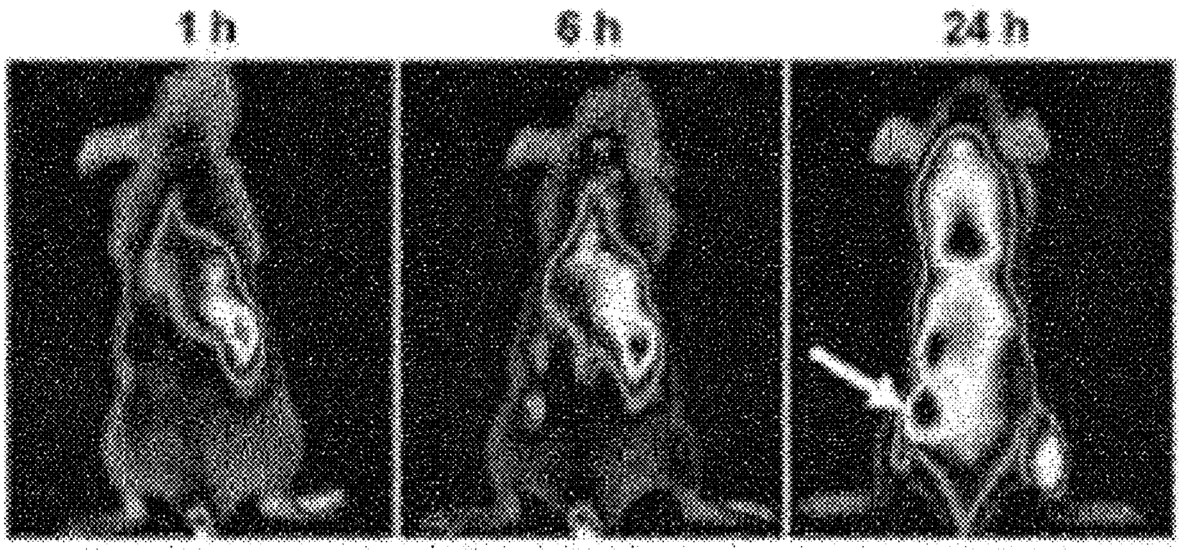
FIG. 9A shows fluorescence images in a tumor model mouse after injecting tRABA nanoparticles loaded with fluorescent IR820.

An experiment was performed to confirm whether tRABA nanoparticles may accumulate in a tumor by binding to GGT overexpressed particularly in cancer cells. FIG. 9A shows fluorescence images taken in a tumor model mouse (a mouse including a tumor) after intravenous injection of tRABA nanoparticles loaded with fluorescent IR820. The tumor exhibited a strong fluorescence signal 24 hours after injecting the tRABA nanoparticles. This shows that the tRABA nanoparticles target tumors by binding to GGT expressed on cancer cells.

Figure 9B:
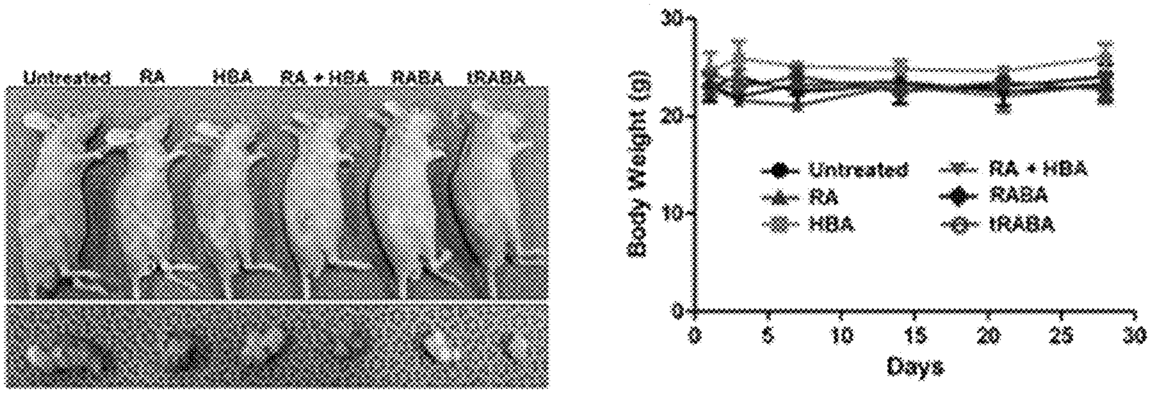
FIG. 9B shows comparison of tumor growth inhibition efficacy of RA, HBA, RA+HBA, and tRABA and body weight change according to treatment with the same.

Next, the anticancer effect was evaluated by administering a therapeutic drug in the tumor model mice when the tumor size reached 50 $mm^3$. A therapeutic drug was intravenously administered on Days 1, 4, 7, 10, and 13 to the tumor model mice. The results are shown in FIG. 9B. According to the results, RA (3 mg/kg), HBA (1.5 mg/kg), and their combination had a negligible inhibitory effect on tumor growth. On the other hand, tRABA (5 mg/kg) almost perfectly inhibited tumor growth without any change in the body weight during the 4-week observation period.

Figure 9C:
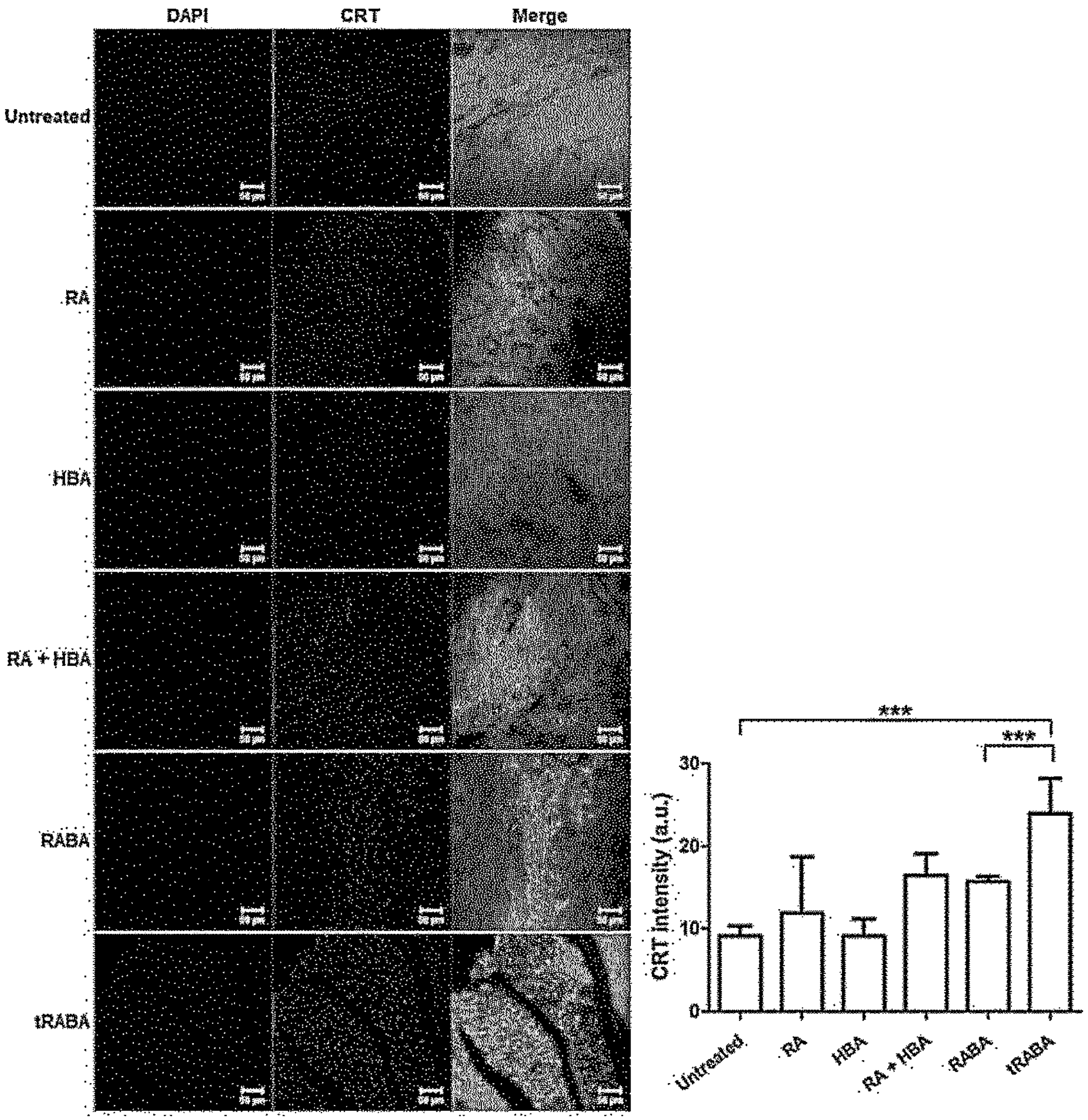
FIG. 9C shows the results of a CRT expression analysis of cancer cells according to treatment with RA, HBA, RA+HBA, RABA, and tRABA.
Figure 9D:
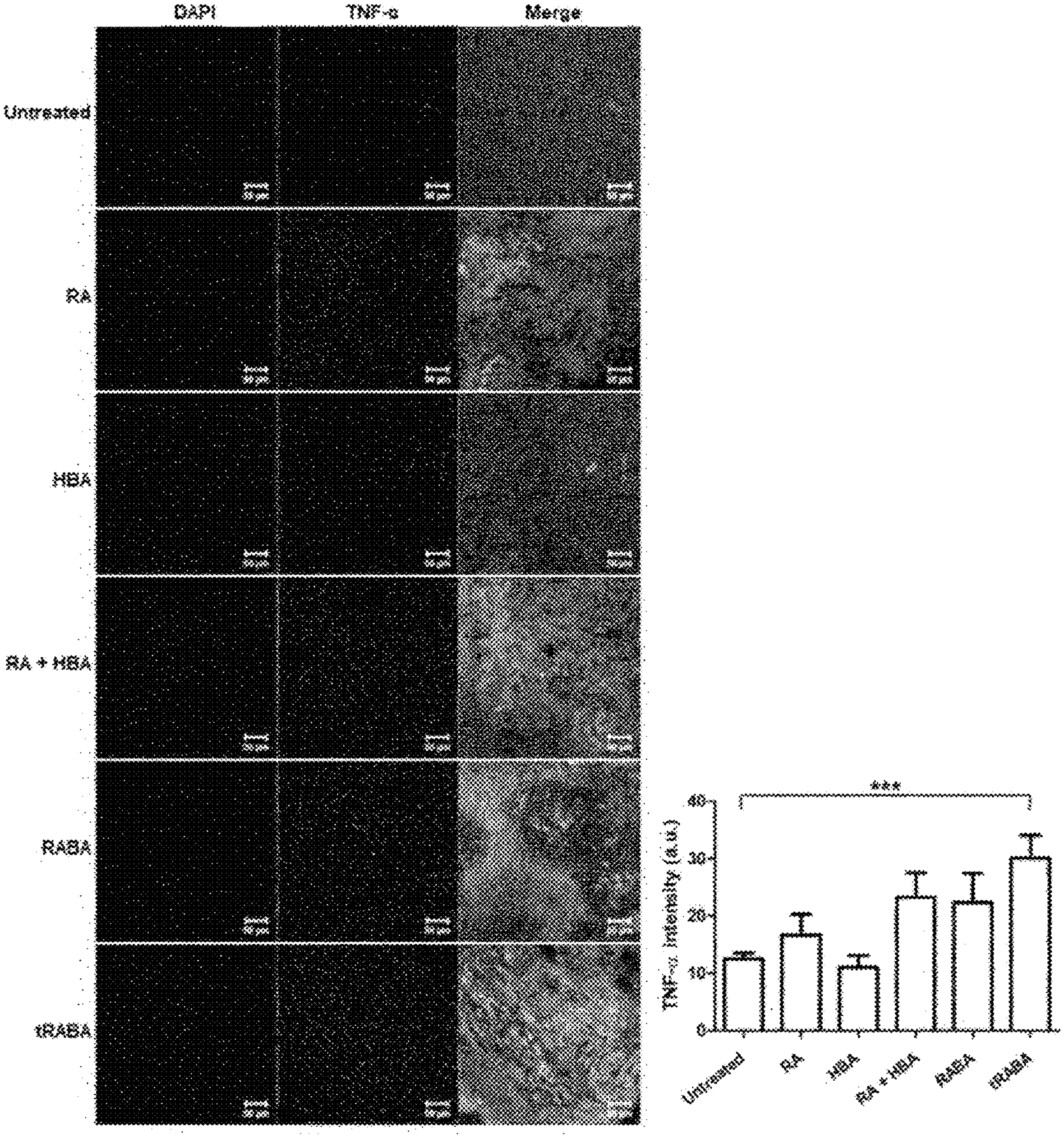
FIG. 9D shows the results of a TNF-α expression analysis of cancer cells according to treatment with RA, HBA, RA+HBA, RABA, and tRABA.

Next, since it is known that TNF-α is released during immunogenic apoptosis and promotes immune responses to exhibit antitumor activity, an experiment for evaluating the CRT and TNF-α levels was performed to confirm whether tRABA nanoparticles induce immunogenic apoptosis in a tumor. As a result, it was confirmed that CRT expression was significantly increased by treatment with tRABA nanoparticles compared to RABA and RA+HBA (FIG. 9*c*), and TNF-α expression was significantly improved (FIG. 9D). In addition, the immunostaining images show that tRABA nanoparticles significantly induce CRT and TNF-α expression in tumors.

Figure 9E:
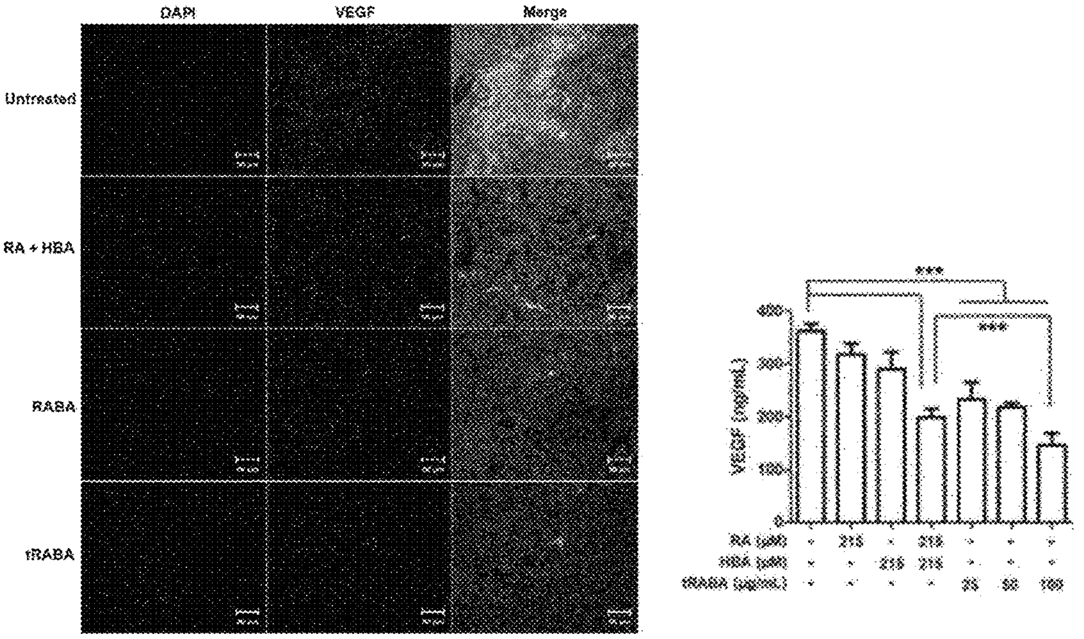
FIG. 9E shows the results of a VEGF expression analysis of cancer cells according to treatment with RA+HBA, RABA, and tRABA.

Next, tumor tissues were examined to evaluate the effect of tRABA nanoparticles on VEGF expression. As shown in FIG. 9E, it was confirmed that the untreated tumors showed high VEGF expression, while RA+BHA inhibited VEGF expression, and the tRABA nanoparticles significantly inhibited VEGF expression.

Figure 9F:
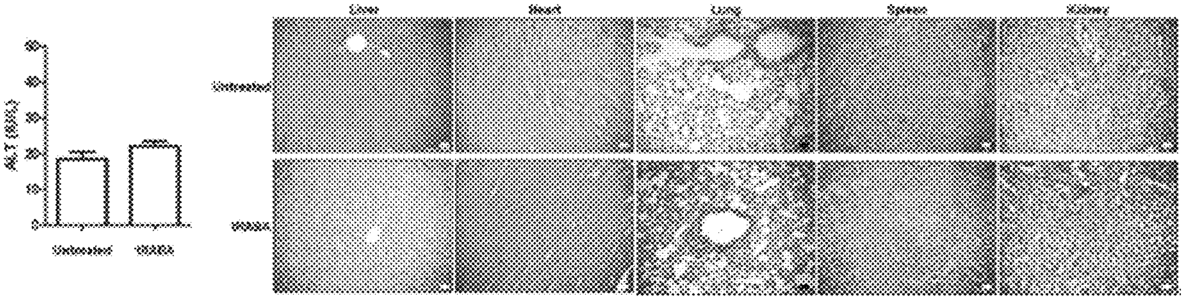
FIG. 9F shows ALT level in serum after tRABA injection and an H&E staining photograph of removed organs after tRABA injection.

Next, to evaluate the safety of tRABA nanoparticles, tRABA was injected into normal mice once every 3 days for 2 weeks. As shown in FIG. 9F, no abnormal change was observed in the level of alanine aminotransferase (ALT) in the serum after tRABA injection, and even in the results of H&E staining of each extracted organ for histological toxicity analysis, no abnormal findings were observed compared to the untreated group. In addition, there was no particular change in the body weight during the two-week observation period. From these results, the safety of tRABA and the expectation to the transfer to clinical practice were confirmed.

INDUSTRIAL APPLICABILITY

The present invention relates to a retinoic acid prodrug and an anticancer drug composition including the same. According to the present invention, retinoic acid can be effectively used for anticancer treatment, the anticancer effect can be maximized, and tumor targeting is possible without a separate drug delivery system.

The invention claimed is:

1. A retinoic acid prodrug (RABA) comprising:

a boron functional group, wherein the RABA has a structure represented by Formula 1:

[Formula 1]

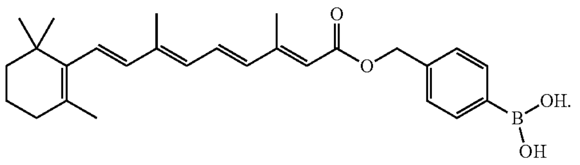

2. The RABA according to claim 1, wherein the RABA forms nanoparticles through self-assembly.

3. The RABA according to claim 2, wherein the nanoparticles are formed by nano-precipitating the RABA in a solvent.

4. The RABA according to claim 2, wherein the nanoparticles are composed of 100% by weight of the RABA.

5. The RABA according to claim 2, wherein surfaces of the nanoparticles are coated with γ-polyglutamic acid (γPGA).

6. The RABA according to claim 5, wherein the nanoparticles target cancer cells in which gamma glutamyl transferase (GGT) is overexpressed.

7. The RABA according to claim 1, wherein the RABA produces quinone methide (QM) in the presence of H2O2.

8. The RABA according to claim 1, wherein the RABA produces hydroxybenzyl alcohol (HBA) in presence of H2O2.

9. The RABA according to claim 1, wherein the RABA depletes H2O2 and glutathione (GSH).

10. The RABA according to claim 1, wherein the RABA inhibits tumor growth.

11. An anticancer composition comprising the RABA according to claim 1 as an active ingredient.

* * * * *